United States Patent
Kim et al.

(10) Patent No.: US 12,146,023 B2
(45) Date of Patent: Nov. 19, 2024

(54) METHOD FOR MANUFACTURING DIISOCYANATE AND OPTICAL LENS

(71) Applicant: WOORI FINE CHEM CO., LTD., Gyeonggi-do (KR)

(72) Inventors: Dal Seong Kim, Gyeonggi-do (KR); Oh Joon Kwon, Gyeonggi-do (KR); Sung Gi Lee, Gyeonggi-do (KR); Gyeong Ha Choi, Chungcheongbuk-do (KR); Junghwan Shin, Seoul (KR)

(73) Assignee: WOORI FINE CHEM CO., LTD., Gyeonggi-do (KR)

( * ) Notice: Subject to any disclaimer, the term of this patent is extended or adjusted under 35 U.S.C. 154(b) by 769 days.

(21) Appl. No.: 15/734,645

(22) PCT Filed: Jun. 5, 2019

(86) PCT No.: PCT/KR2019/006832
§ 371 (c)(1),
(2) Date: Dec. 3, 2020

(87) PCT Pub. No.: WO2019/235862
PCT Pub. Date: Dec. 12, 2019

(65) Prior Publication Data
US 2021/0230352 A1  Jul. 29, 2021

(30) Foreign Application Priority Data

Jun. 7, 2018 (KR) .......... 10-2018-0065666
Jun. 7, 2018 (KR) .......... 10-2018-0065667
Jun. 7, 2018 (KR) .......... 10-2018-0065668

(51) Int. Cl.
*C08G 18/76* (2006.01)
*C07C 263/10* (2006.01)
*C08F 2/06* (2006.01)
*G02B 1/04* (2006.01)

(52) U.S. Cl.
CPC ........ *C08G 18/7642* (2013.01); *C07C 263/10* (2013.01); *C08F 2/06* (2013.01); *G02B 1/041* (2013.01)

(58) Field of Classification Search
CPC ..... C07C 265/14; C07C 263/10; G02B 1/041; C08G 18/72; C08G 18/764
See application file for complete search history.

(56) References Cited

U.S. PATENT DOCUMENTS 3,492,331 A * 1/1970 Ulrich .............. C07C 263/10
548/569
2017/0210702 A1  7/2017 Halpaap et al.

FOREIGN PATENT DOCUMENTS

| | | |
|---|---|---|
| CN | 1931834 A | 3/2007 |
| CN | 106674056 A | 5/2017 |
| CN | 106748887 A | 5/2017 |
| JP | 2790513 B2 | 8/1998 |
| JP | 2018-070611 A | 5/2018 |
| KR | 1994-0001948 B1 | 3/1994 |
| KR | 10-2012-0076329 A | 7/2012 |
| KR | 10-1842254 B1 | 3/2018 |
| WO | 2017/174765 A1 | 10/2017 |
| WO | 2017/179575 A1 | 10/2017 |

OTHER PUBLICATIONS

Office Action issued by Korean Patent Office on Dec. 23, 2020.
Office Action issued by the Korean Intellectual Property Office on Oct. 27, 2021.

* cited by examiner

*Primary Examiner* — Gregory Listvoyb
(74) *Attorney, Agent, or Firm* — IP & T GROUP LLP

(57) ABSTRACT

Provided is a method for manufacturing diisocyanate and an optical lens in which, during the manufacture of diisocyanate from diamine via diamine hydrochloride, use is made of an aqueous hydrochloric acid solution and an organic solvent instead of hydrogen chloride gas and solid-phase triphosgen instead of phosgen gas while reaction conditions are controlled, whereby the diisocyanate of high quality can be manufactured at excellent yield, with the causation of less environmental problems.

14 Claims, 1 Drawing Sheet

[Fig. 1]
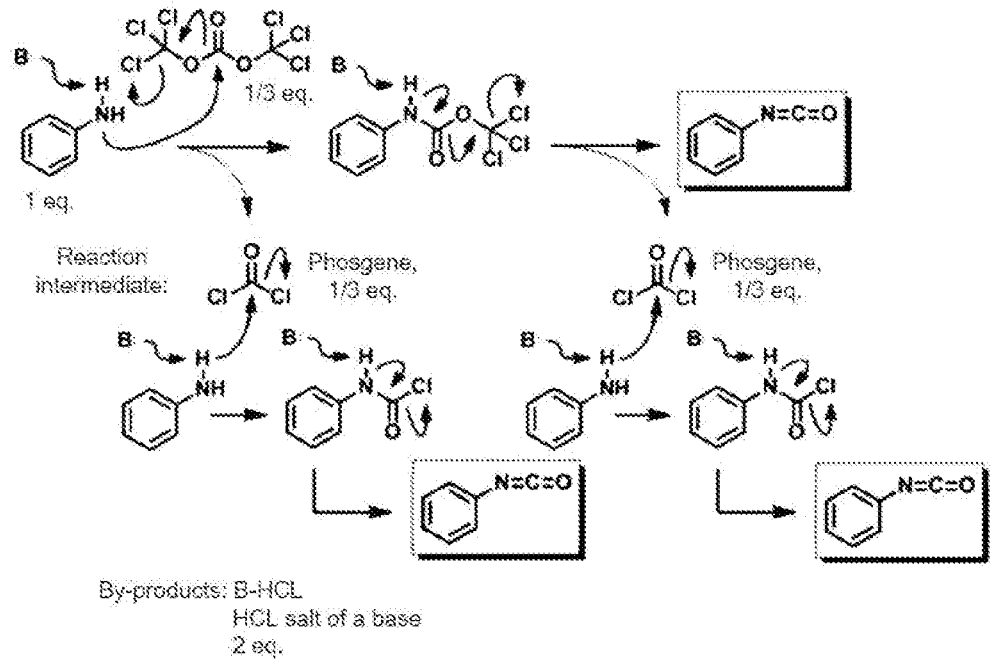
[Fig. 2]
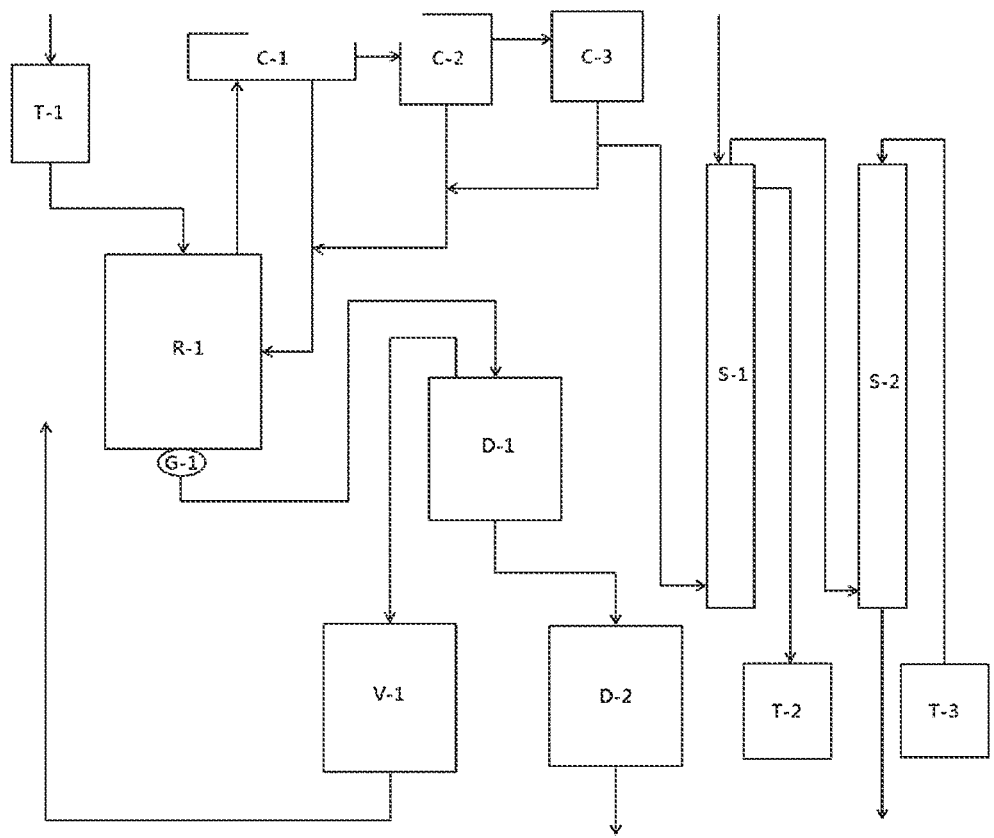

METHOD FOR MANUFACTURING DIISOCYANATE AND OPTICAL LENS

This application is a national stage application of PCT/KR2019/006832 filed on Jun. 5, 2019, which claims priorities of Korean patent application number 10-2018-0065666 filed on Jun. 7, 2018, Korean patent application number 10-2018-0065667 filed on Jun. 7, 2018 and Korean patent application number 10-2018-0065668 filed on Jun. 7, 2018. The disclosure of each of the foregoing applications is incorporated herein by reference in its entirety.

TECHNICAL FIELD

Embodiments relate to processes for preparing a diisocyanate and an optical lens. More specifically, the embodiments relate to a process for preparing a diisocyanate using a diamine hydrochloride. In addition, the embodiments relate to a process for preparing an optical lens using the diisocyanate thus prepared.

BACKGROUND ART

Isocyanates used as a raw material for plastic optical lenses are prepared by a phosgene method, a non-phosgene method, a pyrolysis method, or the like.

In the phosgene method, an amine as a raw material is reacted with phosgene ($COCl_2$) gas to synthesize an isocyanate. In addition, in the non-phosgene method, xylylene chloride is reacted with sodium cyanate in the presence of a catalyst to synthesize an isocyanate. In the pyrolysis method, an amine is reacted with an alkyl chloroformate to prepare a carbamate, which is pyrolyzed in the presence of a catalyst at a high temperature to synthesize an isocyanate.

The phosgene method among the above methods for preparing isocyanates is the most widely used. In particular, a direct method in which an amine is directly reacted with phosgene gas has been commonly used. But it has a problem that a plurality of apparatuses for the direct reaction of phosgene gas are required. Meanwhile, in order to supplement the direct method, a hydrochloride method has been developed in which an amine is reacted with hydrogen chloride gas to obtain an amine hydrochloride as an intermediate, which is reacted with phosgene, as disclosed in Korean Patent Publication No. 1994-1948.

DISCLOSURE OF INVENTION

Technical Problem

In the method of obtaining hydrochloride as an intermediate by reacting an amine with hydrogen chloride gas among the conventional phosgene methods for synthesizing isocyanates, a hydrochloride is produced as fine particles at atmospheric pressure, so that the agitation inside the reactor is not smoothly carried out. Thus, an additional process of raising the temperature to increase the pressure inside the reactor is required, and there is a problem that the yield of the final product is low as well.

Thus, an attempt has been made to obtain a hydrochloride using an aqueous hydrochloric acid solution instead of hydrogen chloride gas. However, as the amine is dissolved in the aqueous hydrochloric acid solution, the yield was significantly reduced to 50%, making it difficult to be applied in practice. There is a difficulty in that an amine having a low content of water and impurities should be used as a raw material in order to increase the purity of the final product.

In particular, phosgene gas used in the conventional phosgene method is highly toxic and is a substance subject to environmental regulations. There is a difficulty in storage and management since a separate cooling apparatus is required to store it.

Accordingly, as a result of the research conducted by the present inventors, it has been discovered that it is possible to solve the conventional environmental, yield, and quality problems in the process of preparing a diisocyanate, which is mainly used as a raw material for plastic optical lenses, from a diamine through a hydrochloride thereof by way of using an aqueous hydrochloric acid solution and an organic solvent instead of hydrogen chloride gas and solid triphosgene instead of phosgene gas while adjusting the reaction conditions.

Accordingly, an object of the embodiments is to provide processes for preparing a diisocyanate and an optical lens having excellent yield and quality while reducing the environmental problems.

Solution to Problem

According to an embodiment of the present invention, there is provided a process for preparing a diisocyanate, which comprises preparing at least one diamine selected from the group consisting of orthoxylylenediamine, metaxylylenediamine, paraxylylenediamine, norbornenediamine, hydrogenated xylylenediamine, and isophoronediamine; reacting the diamine with an aqueous hydrochloric acid solution in a first solvent to obtain a diamine hydrochloride; and reacting the diamine hydrochloride with triphosgene in a second organic solvent to obtain a diisocyanate.

According to another embodiment of the present invention, there is provided a process for preparing metaxylylene diisocyanate, which comprises reacting metaxylylenediamine with an aqueous hydrochloric acid solution in a first solvent to obtain metaxylylenediamine hydrochloride; and reacting the metaxylylenediamine hydrochloride with triphosgene in a second organic solvent to obtain metaxylylene diisocyanate.

According to still another embodiment of the present invention, there is provided a process for preparing an optical lens, which comprises preparing at least one diamine selected from the group consisting of orthoxylylenediamine, metaxylylenediamine, paraxylylenediamine, norbornenediamine, hydrogenated xylylenediamine, and isophoronediamine; reacting the diamine with an aqueous hydrochloric acid solution in a first solvent to obtain a diamine hydrochloride; reacting the diamine hydrochloride with triphosgene in a second organic solvent to obtain a diisocyanate; and mixing the diisocyanate with a thiol or an episulfide and polymerizing and curing the resultant in a mold.

Advantageous Effects of Invention

In the process for preparing a diisocyanate according to the above embodiment, phosgene gas, which is highly toxic and has difficulties in storage and management, is not used. Instead, triphosgene, which is less toxic and does not require a separate cooling storage apparatus since it is solid at room temperature, is used; thus, it is excellent in the handling convenience and processability.

In addition, in the process for preparing a diisocyanate according to the above embodiment, an aqueous hydrochloric acid solution, without the use of hydrogen chloride gas, is used to prepare a diamine hydrochloride as an intermediate Since the reaction can be carried out even at atmospheric pressure, an additional apparatus for high-temperature heating and cooling is not required, and the yield can be enhanced.

In addition, in the process for preparing a diisocyanate according to the above embodiment, an aqueous hydrochloric acid solution and an organic solvent are used, while the reaction conditions are adjusted, to prepare a diamine hydrochloride, so that the final yield can be further enhanced by preventing the hydrochloride from being dissolved in the aqueous hydrochloric acid solution. The selection of raw materials can be broadened since the content of water and impurities in the raw material diamine has little impact.

Thus, the process for preparing a diisocyanate according to the embodiment can be applied to the preparation of a plastic optical lens of high quality.

BRIEF DESCRIPTION OF DRAWING

FIG. 1 shows an example of the mechanism by which metaxylylene diisocyanate is produced through a reaction between metaxylylenediamine hydrochloride and triphosgene.

FIG. 2 shows an example of the process equipment for the reaction of metaxylylenediamine hydrochloride and triphosgene.

REFERENCE NUMERALS OF THE DRAWINGS

T-1: first tank, T-2: second tank, T-3: third tank
R-1: reactor, D-1: first distiller, D-2: second distiller
C-1: first condenser, C-2: second condenser, C-3: third condenser
S-1: first scrubber, S-2: second scrubber
G-1: viewing window, V-1: solvent recovery apparatus.

BEST MODE FOR CARRYING OUT THE INVENTION

Throughout the present specification, when a part is referred to as "comprising" an element, it is understood that other elements may be comprised, rather than other elements are excluded, unless specifically stated otherwise.

In addition, all numbers and expression related to the physical properties, contents, dimensions, and the like used herein are to be understood as being modified by the term "about," unless otherwise indicated.

In the present specification, an "amine" refers to a compound having one or more amine groups at the terminal, and a "diamine" refers to a compound having two amine groups at the terminal. They may have a wide variety of structures depending on the skeleton of an aliphatic chain, an aliphatic ring, and an aromatic ring. Specific examples of the diamine include orthoxylylenediamine, metaxylylenediamine, paraxylylenediamine, hexamethylenediamine, 2,2-dimethylpentanediamine, 2,2,4-trimethylhexanediamine, butenediamine, 1,3-butadiene-1,4-diamine, 2,4,4-trimethylhexamethylenediamine, bis(aminoethyl)carbonate, bis(aminoethyl) ether, lysine diaminomethyl ester, bis(aminoethyl)benzene, bis(aminopropyl)benzene, α,α,α',α'-tetramethylxylylenediamine, bis(aminobutyl)benzene, bis(aminomethyl)naphthalene, bis(aminomethyl)diphenyl ether, bis(aminoethyl)phthalate, 2,6-di(aminomethyl)furan, bis(aminomethyl)cyclohexane, dicyclohexylmethanediamine, cyclohexanediamine, methylcyclohexanediamine, dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl)tricyclodecane, 4,8-bis(aminomethyl)tricyclodecane, 4,9-bis(aminomethyl)tricyclodecane, bis(aminomethyl)norbornene, bis(aminomethyl) sulfide, bis(aminoethyl) sulfide, bis(aminopropyl) sulfide, bis(aminohexyl) sulfide, bis(aminomethyl) sulfone, bis(aminomethyl) disulfide, bis(aminoethyl) disulfide, bis(aminopropyl) disulfide, bis(aminomethylthio)methane, bis(aminoethylthio)methane, bis(aminoethylthio)ethane, and bis(aminomethylthio)ethane.

In the present specification, an "isocyanate" refers to a compound having an NCO group, a "diisocyanate" refers to a compound having two NCO groups at the terminal. They may have a wide variety of structures depending on the skeleton of an aliphatic chain, an aliphatic ring, and an aromatic ring. Specific examples of the diamine include orthoxylylene diisocyanate, metaxylylene diisocyanate, paraxylylene diisocyanate, hexamethylene diisocyanate, 2,5-bis(isocyanatomethyl)-bicyclo[2.2.1]heptane, 2,6-bis(isocyanatomethyl)-bicyclo[2.2.1]heptane, bis(isocyanatomethyl)cyclohexane, dicyclohexylmethane diisocyanate, isophorone diisocyanate, 1,2-diisocyanatobenzene, 1,4-diisocyanatobenzene, 2,4-diisocyanatotoluene, 1,3-diisocyanatobenzene, ethylphenylene diisocyanate, dimethylphenylene diisocyanate, biphenyl diisocyanate, toluidine diisocyanate, 4,4'-methylenebis(phenylisocyanate), 1,2-bis(isocyanatomethyl)benzene, 1,3-bis(isocyanatomethyl)benzene, 1,4-bis(isocyanatomethyl)benzene, 1,2-bis(isocyanatoethyl)benzene, 1,3-bis(isocyanatoethyl)benzene, 1,4-bis(isocyanatoethyl)benzene, α,α,α',α'-tetramethylxylylene diisocyanate, bis(isocyanatomethyl)naphthalene, bis(isocyanatomethylphenyl) ether, bis(isocyanatomethyl) sulfide, bis(isocyanatoethyl) sulfide, bis(isocyanatopropyl) sulfide, 2,5-diisocyanatotetrahydrothiophene, 2,5-diisocyanatomethyltetrahydrothiophene, 3,4-diisocyanatomethyltetrahydrothiophene, 2,5-diisocyanato-1,4-dithiane, and 2,5-diisocyanatomethyl-1,4-dithiane.

[Process for Preparing a Diisocyanate]

The process for preparing a diisocyanate according to an embodiment comprises preparing at least one diamine selected from the group consisting of orthoxylylenediamine, metaxylylenediamine, paraxylylenediamine, norbornenediamine, hydrogenated xylylenediamine, and isophoronediamine; reacting the diamine with an aqueous hydrochloric acid solution in a first solvent to obtain a diamine hydrochloride; and reacting the diamine hydrochloride with triphosgene in a second organic solvent to obtain a diisocyanate.

In the process for preparing a diisocyanate according to an embodiment, the diamine used as a raw material may be at least one selected from the group consisting of orthoxylylenediamine (o-XDA), metaxylylenediamine (m-XDA), paraxylylenediamine (p-XDA, norbornenediamine (NBDA), hydrogenated xylylenediamine (H6XDA), and isophoronediamine (IPDA).

Preparation of a Diamine Hydrochloride

First, a diamine is reacted with an aqueous hydrochloric acid solution in a first organic solvent to obtain a diamine hydrochloride.

In the conventional method in which hydrogen chloride gas is used, a hydrochloride is produced as fine particles upon reaction at atmospheric pressure, so that the agitation inside the reactor is not smoothly carried out. Thus, an additional process of raising the pressure to increase the internal temperature of the reactor is required, and there is a problem that the yield of the final product is low as well.

According to the above embodiment, however, since an aqueous hydrochloric acid solution is used, it is possible to solve the problem involved in the prior art in which hydrogen chloride gas is used. Specifically, when an aqueous hydrochloric acid solution is used, the product obtained through the reaction is in a solid form rather than a slurry form, so that the yield is high. The reaction can be carried out even at atmospheric pressure, so that a separate apparatus or process for rapid cooling is not required.

The concentration of the aqueous hydrochloric acid solution may be 5% by weight to 50% by weight. Within the above concentration range, it is possible to minimize the dissolution of the hydrochloride in the aqueous hydrochloric acid solution, thereby enhancing the final yield, and to improve the handling convenience.

Specifically, the concentration of the aqueous hydrochloric acid solution may be 10% by weight to 45% by weight, 20% by weight to 45% by weight, or 30% by weight to 40% by weight. More specifically, the aqueous hydrochloric acid solution may have a concentration of 20% by weight to 45% by weight.

The diamine and the aqueous hydrochloric acid solution may be introduced to the reaction at an equivalent ratio of 1:2 to 5. If the equivalent ratio is within the above range, it is possible to reduce the unreacted materials and to prevent the reduction in the yield caused by dissolution as water is generated. Specifically, the diamine and the aqueous hydrochloric acid solution may be introduced to the reaction at an equivalent ratio of 1:2 to 2.5.

The introduction of the diamine and the aqueous hydrochloric acid solution may be carried out while the internal temperature of the reactor is maintained to be constant.

When the diamine and the hydrochloric acid aqueous solution are introduced, the internal temperature of the reactor may be in the range of 20° C. to 100° C. Within the above temperature range, it is possible to prevent the temperature being raised above the boiling point, which is not suitable for the reaction, or the temperature being lowered too much, whereby the reaction efficiency is reduced.

Specifically, when the diamine and the hydrochloric acid aqueous solution are introduced, the internal temperature of the reactor may be 20° C. to 60° C. or 20° C. to 40° C.

More specifically, the diamine and the hydrochloric acid solution may be introduced to the reaction at an equivalent ratio of 1:2 to 5 at a temperature of 20° C. to 40° C.

In the conventional hydrochloride method, a large amount of heat is generated in the reaction, which requires rapid cooling through a separate cooler, whereas the reaction materials are introduced while a low temperature is maintained according to the embodiment, which does not require a separate cooler.

The introduction of the diamine and the aqueous hydrochloric acid solution may be carried out, for example, in a sequence in which the hydrochloric acid aqueous solution may be first introduced to the reactor and the diamine may then be slowly introduced to the reactor. The introduction of the diamine and/or the aqueous hydrochloric acid solution may be carried out for 30 minutes to 1 hour.

When the introduction of the diamine and the hydrochloric acid aqueous solution is completed, the internal temperature of the reactor may be lowered to 0° C. to 20° C., 0° C. to 10° C., or 10° C. to 20° C.

The reaction between the diamine and the aqueous hydrochloric acid solution may be carried out at atmospheric pressure for, for example, 30 minutes to 2 hours with stirring.

Thereafter, the first organic solvent may be introduced to the reaction, which is cooled and further stirred to carry out the reaction.

The first organic solvent may be a hydrophilic solvent. Specifically, it may be at least one selected from the group consisting of diethyl ether, diisopropyl ether, dioxane, tetrahydrofuran, methanol, ethanol, dimethyl sulfoxide, dimethylformamide, acetonitrile, acetone, trichloroethylene, tetrachloroethane, trichloroethane, n-butanol, isobutanol, methyl ethyl ketone, methyl butyl ketone, isopropanol, and methyl acetate.

The amount (weight) of the first organic solvent introduced may be 1 to 5 times the weight of the diamine. If the introduced amount is within the above range, it is possible to prevent the use of excessive organic solvents while the yield of the final hydrochloride is high. Specifically, the first organic solvent may be introduced to the reaction in an amount of 1 to 2 times, or 1 to 1.5 times, the weight of the diamine.

After the first organic solvent is introduced, the cooling temperature may be −10° C. to 10° C. or −5° C. to 5° C. In addition, the additional reaction time after cooling may be 30 minutes to 2 hours or 30 minutes to 1 hour.

According to a specific example, the reaction of the diamine and the aqueous hydrochloric acid solution may sequentially comprise (1a) introducing the aqueous hydrochloric acid solution to a first reactor; (1b) further introducing the diamine to the first reactor and stirring them; and (1c) further introducing the first organic solvent to the first reactor and stirring them.

More specifically, the reaction of the diamine and the aqueous hydrochloric acid solution may further comprise cooling the inside of the reactor to a temperature of 0° C. to 10° C. after the introduction of the diamine and before stirring in step (1b); and cooling the inside of the reactor to a temperature of −5° C. to 5° C. after the introduction of the first organic solvent and before stirring in step (1c).

The reactant obtained through the reaction may be further subjected to separation, filtration, and drying. For example, the aqueous layer may be separated from the reactant, filtered, and dried to obtain a solid diamine hydrochloride. Specifically, the process for preparing a diisocyanate may further comprise removing the impurities generated in the step of obtaining the diamine hydrochloride together with the first organic solvent. Impurities are generated in the reaction for preparing the diamine hydrochloride and are contained in the first organic solvent. Such impurities may be removed by the step of removing the first organic solvent, whereby the purity of the product may be increased.

The yield of the diamine hydrochloride thus obtained may be 80% or more, 85% or more, or 90% or more, specifically 85% to 95% or 88% to 92%. In addition, the water content of the diamine hydrochloride thus obtained may be 5% or less. If it exceeds 5%, the physical properties of the lens finally prepared are not good. As an example, the diamine hydrochloride may be obtained in a yield of 80% or more and a water content of 5% or less.

Meanwhile, the organic layer can be separated from the reactant and recycled as an organic solvent. Thus, the recovery rate of the first organic solvent may be 80% or more, 85% or more, or 90% or more, specifically 80% to 95% or 80% to 82%.

Preparation of a Diisocyanate

Next, the diamine hydrochloride is reacted with triphosgene in a second organic solvent to obtain a diisocyanate.

Specifically, the diamine hydrochloride prepared above is introduced to an organic solvent, reacted with triphosgene (BTMC, bis(trichloromethyl)carbonate), and then filtered and distilled to obtain a diisocyanate.

Specifically, the second organic solvent may be at least one selected from the group consisting of benzene, toluene, ethylbenzene, chlorobenzene, monochlorobenzene, 1,2-dichlorobenzene, dichloromethane, 1-chloro-n-butane, 1-chloro-n-pentane, 1-chloro-n-hexane, chloroform, carbon tetrachloride, n-pentane, n-hexane, n-heptane, n-octane, cyclohexane, cyclopentane, cyclooctane, and methylcyclohexane.

The amount (weight) of the second organic solvent introduced may be 1 to 5 times the weight of the diamine hydrochloride. If the introduced amount is within the above range, it is possible to prevent the use of excessive organic solvents while the yield of the final diisocyanate is high. Specifically, the second organic solvent may be introduced to the reaction in an amount of 2 to 5 times, or 3 to 5 times, the weight of the diamine hydrochloride.

The reaction temperature of the diamine hydrochloride and triphosgene may be 130 to 160° C. If the reaction temperature is within the above range, the reaction between the diamine hydrochloride and triphosgene can be smoothly carried out, and it is possible to suppress the generation of impurities such as tar when the final diisocyanate is produced. Specifically, the reaction temperature of the diamine hydrochloride and triphosgene may be 135° C. to 155° C.

The reaction of the diamine hydrochloride with triphosgene may be carried out for 5 hours to 100 hours. When the reaction time is within the above range, the reaction time is not excessive, and the production of unreacted materials due to the generation of phosgene can be minimized. Specifically, the reaction of the diamine hydrochloride with triphosgene may be carried out for 15 hours to 40 hours, 20 hours to 35 hours, or 24 hours to 30 hours.

As a specific example, the reaction of the diamine hydrochloride with triphosgene may be carried out at a temperature of 130° C. to 160° C. for 5 hours to 100 hours.

The diamine hydrochloride and triphosgene may be introduced to the reaction at an equivalent ratio of 1:1 to 5. When the equivalent ratio is within the above range, the reaction efficiency is high, and it is possible to prevent an increase in reaction time due to an excessive introduction. Specifically, the diamine hydrochloride and triphosgene may be introduced to the reaction at an equivalent ratio of 1:1.5 to 4 or 1:2 to 2.5.

According to a specific example, the reaction of the diamine hydrochloride and triphosgene may sequentially comprise (2a) introducing the second organic solvent to a second reactor; (2b) further introducing the diamine hydrochloride to the second reactor and stirring them; and (2c) further introducing triphosgene to the second reactor and stirring them.

More specifically, the introduction of triphosgene in step (2c) may be carried out by introducing a solution in which triphosgene is dissolved in the same solvent as the second organic solvent to the reactor as divided into two or more times at a temperature of 135° C. to 155° C. for a total of 25 hours to 40 hours.

In such event, the time for each introduction of the triphosgene solution may be 5 hours to 25 hours or 10 hours to 14 hours.

In addition, the time for further reaction by stirring after the introduction of triphosgene may be 2 hours to 5 hours or 3 hours to 4 hours.

Upon the reaction, the reactant may be cooled at a temperature of 90° C. to 110° C.

The reactant obtained through the reaction may be further subjected to separation, filtration, and distillation.

The distillation may comprise first distillation and second distillation.

As a specific example, the diisocyanate may be obtained as a result of subjecting the resultant of the reaction of the diamine hydrochloride and the triphosgene to first distillation at 40° C. to 60° C. for 2 to 8 hours and second distillation at 100° C. to 120° C. for 2 to 10 hours.

The first distillation may be carried out at 0.5 Torr or less, and the second distillation may be carried out at 0.1 Torr or less.

The organic solvent may be recovered and recycled through the first distillation, and a final diisocyanate may be obtained through the second distillation.

Specifically, the diisocyanate may be at least one selected from the group consisting of orthoxylylene diisocyanate (o-XDI), metaxylylene diisocyanate (m-XDI), paraxylylene diisocyanate (p-XDI), norbornene diisocyanate (NBDI), hydrogenated xylylene diisocyanate (H6XDI), and isophorone diisocyanate (IPDI).

The yield of the diisocyanate thus obtained may be 80% or more, 85% or more, or 90% or more. In addition, the purity of the diisocyanate thus obtained may be 95% or more, 99.5% or more, or 99.8% or more.

As a specific example, the diisocyanate may be at least one selected from the group consisting of orthoxylylene diisocyanate, metaxylylene diisocyanate, paraxylylene diisocyanate, norbornene diisocyanate, hydrogenated xylylene diisocyanate, and isophorone diisocyanate, and may have a purity of 99.5% or more.

According to the process of the above embodiment, the yield of diisocyanate is high, the recycling rate of organic solvents is excellent, it is environmentally friendly since highly toxic phosgene gas is not used, it is possible to react at atmospheric pressure, and a separate apparatus for pressurization or rapid cooling is not required.

[Process for Preparing Metaxylylene Diisocyanate]

The process for preparing metaxylylene diisocyanate according to an embodiment comprises reacting metaxylylenediamine with an aqueous hydrochloric acid solution in a first solvent to obtain metaxylylenediamine hydrochloride; and reacting the metaxylylenediamine hydrochloride with triphosgene in a second organic solvent to obtain metaxylylene diisocyanate.

In the process for preparing a diisocyanate according to an embodiment, the diamine used as a raw material is metaxylylenediamine (m-XDA).

Preparation of Metaxylylene Hydrochloride

First, metaxylylenediamine is reacted with an aqueous hydrochloric acid solution in a first organic solvent to obtain metaxylylene hydrochloride.

The following Reaction Scheme 1 shows an example of the reaction in this step.

[Reaction Scheme 1]

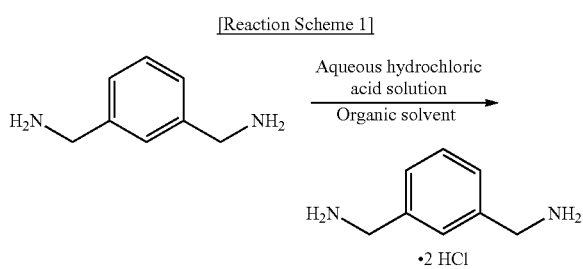

In the conventional method in which hydrogen chloride gas is used, a hydrochloride is produced as fine particles upon reaction at atmospheric pressure, so that the agitation inside the reactor is not smoothly carried out. Thus, an additional process of raising the pressure to increase the internal temperature of the reactor is required, and there is a problem that the yield of the final product is low as well.

According to the above embodiment, however, since an aqueous hydrochloric acid solution is used, it is possible to solve the problem involved in the prior art in which hydrogen chloride gas is used. Specifically, when an aqueous hydrochloric acid solution is used, the product obtained through the reaction is in a solid form rather than a slurry form, so that the yield is high. The reaction can be carried out even at atmospheric pressure, so that a separate apparatus or process for rapid cooling is not required.

The concentration of the aqueous hydrochloric acid solution may be 5% by weight to 50% by weight. Within the above concentration range, it is possible to minimize the dissolution of the hydrochloride in the aqueous hydrochloric acid solution, thereby enhancing the final yield, and to improve the handling convenience.

Specifically, the concentration of the aqueous hydrochloric acid solution may be 10% by weight to 45% by weight, 20% by weight to 45% by weight, or 30% by weight to 40% by weight. More specifically, the aqueous hydrochloric acid solution may have a concentration of 20% by weight to 45% by weight.

The metaxylylenediamine and the aqueous hydrochloric acid solution may be introduced to the reaction at an equivalent ratio of 1:2 to 5. If the equivalent ratio is within the above range, it is possible to reduce the unreacted materials and to prevent the reduction in the yield caused by dissolution as water is generated. Specifically, the metaxylylenediamine and the aqueous hydrochloric acid solution may be introduced to the reaction at an equivalent ratio of 1:2 to 2.5.

The introduction of the metaxylylenediamine and the aqueous hydrochloric acid solution may be carried out while the internal temperature of the reactor is maintained to be constant.

When the metaxylylenediamine and the hydrochloric acid aqueous solution are introduced, the internal temperature of the reactor may be in the range of 20° C. to 100° C. Within the above temperature range, it is possible to prevent the temperature being raised above the boiling point, which is not suitable for the reaction, or the temperature being lowered too much, whereby the reaction efficiency is reduced.

Specifically, when the metaxylylenediamine and the hydrochloric acid aqueous solution are introduced, the internal temperature of the reactor may be 20° C. to 60° C. or 20° C. to 40° C.

More specifically, the metaxylylenediamine and the aqueous hydrochloric acid solution may be introduced to the reaction at an equivalent ratio of 1:2 to 5 at a temperature of 20° C. to 40° C.

In the conventional hydrochloride method, a large amount of heat is generated in the reaction, which requires rapid cooling through a separate cooler, whereas the reaction materials are introduced while a low temperature is maintained according to the embodiment, which does not require a separate cooler.

The introduction of the metaxylylenediamine and the aqueous hydrochloric acid solution may be carried out, for example, in a sequence in which the hydrochloric acid aqueous solution may be first introduced to the reactor and the metaxylylenediamine may then be slowly introduced to the reactor. The introduction of the metaxylylenediamine and/or the aqueous hydrochloric acid solution may be carried out for 30 minutes to 1 hour.

When the introduction of the metaxylylenediamine and the hydrochloric acid aqueous solution is completed, the internal temperature of the reactor may be lowered to 0° C. to 20° C., 0° C. to 10° C., or 10° C. to 20° C.

The reaction between the metaxylylenediamine and the aqueous hydrochloric acid solution may be carried out at atmospheric pressure for, for example, 30 minutes to 2 hours with stirring.

Thereafter, the first organic solvent may be introduced to the reaction, which is cooled and further stirred to carry out the reaction.

The first organic solvent may be a hydrophilic solvent. Specifically, it may be at least one selected from the group consisting of diethyl ether, diisopropyl ether, dioxane, tetrahydrofuran, methanol, ethanol, dimethyl sulfoxide, dimethylformamide, acetonitrile, acetone, trichloroethylene, tetrachloroethane, trichloroethane, n-butanol, isobutanol, methyl ethyl ketone, methyl butyl ketone, isopropanol, and methyl acetate.

The amount (weight) of the first organic solvent introduced may be 1 to 5 times the weight of the metaxylylenediamine. If the introduced amount is within the above range, it is possible to prevent the use of excessive organic solvents while the yield of the final hydrochloride is high. Specifically, the first organic solvent may be introduced to the reaction in an amount of 1 to 2 times, or 1 to 1.5 times, the weight of the metaxylylenediamine.

After the first organic solvent is introduced, the cooling temperature may be −10° C. to 10° C. or −5° C. to 5° C. In addition, the additional reaction time after cooling may be 30 minutes to 2 hours or 30 minutes to 1 hour.

According to a specific example, the reaction of the metaxylylenediamine and the aqueous hydrochloric acid solution may sequentially comprise (1a) introducing the aqueous hydrochloric acid solution to a first reactor; (1b) further introducing the metaxylylenediamine to the first reactor and stirring them; and (1c) further introducing the first organic solvent to the first reactor and stirring them.

More specifically, the reaction of the metaxylylenediamine and the aqueous hydrochloric acid solution may further comprise cooling the inside of the reactor to a temperature of 0° C. to 10° C. after the introduction of the metaxylylenediamine and before stirring in step (1b); and cooling the inside of the reactor to a temperature of −5° C. to 5° C. after the introduction of the first organic solvent and before stirring in step (1c).

The reactant obtained through the reaction may be further subjected to separation, filtration, and drying. For example, the aqueous layer may be separated from the reactant, filtered, and dried to obtain a solid metaxylylenediamine hydrochloride. Specifically, the process for preparing metaxylylene diisocyanate may further comprise removing the impurities generated in the step of obtaining the metaxylylenediamine hydrochloride together with the first organic solvent. Impurities are generated in the reaction for preparing the metaxylylenediamine hydrochloride and are contained in the first organic solvent. Such impurities may be removed by the step of removing the first organic solvent, whereby the purity of the product may be increased.

The yield of the metaxylylenediamine hydrochloride thus obtained may be 80% or more, 85% or more, or 90% or more, specifically 85% to 95% or 88% to 92%. In addition, the water content of the metaxylylenediamine hydrochloride thus obtained may be 5% or less. If it exceeds 5%, the physical properties of the lens finally prepared are not good. As an example, the metaxylylenediamine hydrochloride may be obtained in a yield of 80% or more and a water content of 5% or less.

Meanwhile, the organic layer can be separated from the reactant and recycled as an organic solvent. Thus, the recovery rate of the first organic solvent may be 80% or more, 85% or more, or 90% or more, specifically 80% to 95% or 80% to 82%.

Preparation of Metaxylylene Diisocyanate

Next, the metaxylylenediamine hydrochloride is reacted with triphosgene in a second organic solvent to obtain metaxylylene diisocyanate.

The following Reaction Scheme 2 shows an example of the reaction in this step.

[Reaction Scheme 2]

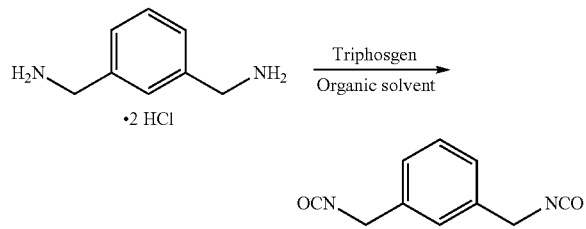

Specifically, the metaxylylenediamine hydrochloride prepared above is introduced to an organic solvent, reacted with triphosgene (BTMC, bis(trichloromethyl)carbonate), and then filtered and distilled to obtain metaxylylene diisocyanate.

Specifically, the second organic solvent may be at least one selected from the group consisting of benzene, toluene, ethylbenzene, chlorobenzene, monochlorobenzene, 1,2-dichlorobenzene, dichloromethane, 1-chloro-n-butane, 1-chloro-n-pentane, 1-chloro-n-hexane, chloroform, carbon tetrachloride, n-pentane, n-hexane, n-heptane, n-octane, cyclohexane, cyclopentane, cyclooctane, and methylcyclohexane.

The amount (weight) of the second organic solvent introduced may be 1 to 5 times the weight of the metaxylylenediamine hydrochloride. If the introduced amount is within the above range, it is possible to prevent the use of excessive organic solvents while the yield of the final metaxylylene diisocyanate is high. Specifically, the second organic solvent may be introduced to the reaction in an amount of 2 to 5 times, or 3 to 5 times, the weight of the metaxylylenediamine hydrochloride.

The reaction temperature of the metaxylylenediamine hydrochloride and triphosgene may be 130 to 160° C. If the reaction temperature is within the above range, the reaction between the metaxylylenediamine hydrochloride and triphosgene can be smoothly carried out, and it is possible to suppress the generation of impurities such as tar when the final metaxylylene diisocyanate is produced. Specifically, the reaction temperature of the metaxylylenediamine hydrochloride and triphosgene may be 135° C. to 155° C.

The reaction of the metaxylylenediamine hydrochloride with triphosgene may be carried out for 5 hours to 100 hours. When the reaction time is within the above range, the reaction time is not excessive, and the production of unreacted materials due to the generation of phosgene can be minimized. Specifically, the reaction of the metaxylylenediamine hydrochloride with triphosgene may be carried out for 15 hours to 40 hours, 20 hours to 35 hours, or 24 hours to 30 hours.

As a specific example, the reaction of the metaxylylenediamine hydrochloride with triphosgene may be carried out at a temperature of 130° C. to 160° C. for 5 hours to 100 hours.

FIG. 1 shows an example of the reaction mechanism by which metaxylylene diisocyanate is produced through a reaction between metaxylylenediamine hydrochloride and triphosgene. As shown in FIG. 1, the amine group of the diamine hydrochloride attacks the carbonate group of the triphosgene. Then, as electrons move, phosgene gas ($COCl_2$) is generated. Through repetition of the above, phosgene gas is continuously generated. As a result, the reaction with the amine group of metaxylylenediamine hydrochloride takes place. In FIG. 1, B may comprise an anion, for example, a chlorine ion.

The metaxylylenediamine hydrochloride and triphosgene may be introduced to the reaction at an equivalent ratio of 1:1 to 5. When the equivalent ratio is within the above range, the reaction efficiency is high, and it is possible to prevent an increase in reaction time due to an excessive introduction. Specifically, the metaxylylenediamine hydrochloride and triphosgene may be introduced to the reaction at an equivalent ratio of 1:1.5 to 4 or 1:2 to 2.5.

According to a specific example, the reaction of the metaxylylenediamine hydrochloride and triphosgene may sequentially comprise (2a) introducing the second organic solvent to a second reactor; (2b) further introducing the metaxylylenediamine hydrochloride to the second reactor and stirring them; and (2c) further introducing triphosgene to the second reactor and stirring them.

More specifically, the introduction of triphosgene in step (2c) may be carried out by introducing a solution in which triphosgene is dissolved in the same solvent as the second organic solvent to the reactor as divided into two or more times at a temperature of 135° C. to 155° C. for a total of 25 hours to 40 hours.

In such event, the time for each introduction of the triphosgene solution may be 5 hours to 25 hours or 10 hours to 14 hours.

In addition, the time for further reaction by stirring after the introduction of triphosgene may be 2 hours to 5 hours or 3 hours to 4 hours.

Upon the reaction, the reactant may be cooled at a temperature of 90° C. to 110° C.

The reactant obtained through the reaction may be further subjected to separation, filtration, and distillation.

The distillation may comprise first distillation and second distillation.

As a specific example, the metaxylylene diisocyanate may be obtained as a result of subjecting the resultant of the reaction of the metaxylylenediamine hydrochloride and the triphosgene to first distillation at 40° C. to 60° C. for 2 to 8 hours and second distillation at 100° C. to 120° C. for 2 to 10 hours.

The first distillation may be carried out at 0.5 Torr or less, and the second distillation may be carried out at 0.1 Torr or less.

The organic solvent may be recovered and recycled through the first distillation, and final metaxylylene diisocyanate may be obtained through the second distillation.

The yield of the metaxylylene diisocyanate thus obtained may be 80% or more, 85% or more, or 90% or more. In addition, the purity of the metaxylylene diisocyanate thus obtained may be 95% or more, 99.5% or more, or 99.8% or more.

According to the process of the above embodiment, the yield of metaxylylene diisocyanate is high, the recycling rate of organic solvents is excellent, it is environmentally friendly since highly toxic phosgene gas is not used, it is possible to react at atmospheric pressure, and a separate apparatus for pressurization or rapid cooling is not required.

Measurement of the Color and Transparency of a Reaction Solution

According to an embodiment, the step of obtaining metaxylylene diisocyanate from the metaxylylenediamine hydrochloride and triphosgene may comprise (i) reacting the metaxylylenediamine hydrochloride with triphosgene in a second organic solvent to obtain a reaction solution; (ii) measuring the color and transparency of the reaction solution; and (iii) obtaining metaxylylene diisocyanate from the reaction solution.

In the reaction of the metaxylylenediamine hydrochloride and triphosgene, the color and transparency of the reaction solution may be measured to adjust the reaction conditions. For example, the reaction solution at the beginning of the reaction may be opaque colorless or white, and the reaction solution at the time when the reaction is ordinarily completed may be transparent or close to transparent in a light brown color.

For example, in the step of measuring the color and transparency of the reaction solution, the reaction solution may have a transparent light brown color.

Specifically, the reaction solution may have an L* value of 45 to 60, an a* value of 3 to 15, and a b* value of 15 to 30 in the CIE-LAB color coordinate. More specifically, the reaction solution may have an L* value of 50 to 55, an a* value of 5 to 10, and a b* value of 20 to 25 in the CIE-LAB color coordinate.

In addition, the reaction solution may have a transmittance of 60% or more, 70% or more, 80% or more, or 90% or more, for light having a wavelength of 550 nm. In addition, the reaction solution may have a haze of 20% or less, 10% or less, 5% or less, or 3% or less. Specifically, the reaction solution may have a transmittance of 70% or more for light having a wavelength of 550 nm and a haze of 10% or less. More specifically, the reaction solution may have a transmittance of 80% or more for light having a wavelength of 550 nm and a haze of 5% or less.

On the other hand, if the reaction of the metaxylylenediamine hydrochloride and triphosgene is not completed, the reaction solution may be opaque or have a precipitate, and the color may be pale, white, or colorless. In addition, if side reactions take place to a significant extent, the reaction solution may be opaque or may have a color other than light brown, for example, a dark brown or dark color.

The reaction of the metaxylylenediamine hydrochloride and triphosgene may be carried out simultaneously with the step of measuring the color and transparency of the reaction solution.

That is, while the reaction of the metaxylylenediamine hydrochloride and triphosgene is being carried out, the color and transparency of the reaction solution may be measured in real time.

In addition, for more accurate measurement, a part of the reaction solution may be collected to precisely measure the color and transparency thereof. For example, the measurement of the color and transparency of the reaction solution may be carried out by collecting a part of the reaction solution and measuring the color and transparency of the collected reaction solution.

In such event, the reaction equivalent, reaction temperature, or reaction time may be adjusted according to the color and transparency of the reaction solution. For example, the timing for terminating the reaction may be determined according to the color and transparency of the reaction solution. That is, step (i) and step (ii) are simultaneously carried out, in which the timing for terminating the reaction of the metaxylylenediamine hydrochloride and triphosgene in step (i) may be determined according to the color and transparency of the reaction solution measured in step (ii). The timing for terminating the reaction may come after when the reaction solution turns a transparent light brown color.

As an example, the reactor may have a viewing window, and the measurement of the color and transparency of the reaction solution may be carried out through the viewing window.

The reactor is connected to one or more stages of condensers. Once the gas generated in the reactor has been transferred to the one or more stages of condensers, the second organic solvent present in the gas may be condensed and recycled to the reactor.

The one or more stages of condensers are connected to a first scrubber and a second scrubber. The gas transferred from the reactor to the one or more stages of condensers contains hydrogen chloride gas and phosgene gas, the first scrubber may dissolve the hydrogen chloride gas in water to produce an aqueous solution, and the second scrubber may neutralize the phosgene gas with an aqueous NaOH solution.

In addition, the reactor is connected to one or more stages of distillers. The reaction solution is transferred to the one or more stages of distillers, and the one or more stages of distillers may separate the metaxylylene diisocyanate and the second organic solvent from the reaction solution.

The separated second organic solvent may be recycled for the reaction of the metaxylylenediamine hydrochloride and triphosgene.

FIG. 2 shows an example of the process equipment for the reaction of metaxylylenediamine hydrochloride and triphosgene.

First, a first tank (T-1) is charged with a second organic solvent and triphosgene, and the temperature is maintained to be constant by refluxing hot water. The inside of a reactor (R-1) is purged with nitrogen, a second organic solvent is introduced thereto with stirring, metaxylylenediamine hydrochloride is slowly introduced thereto, and they are stirred while the internal temperature of the reactor is maintained to be constant.

Thereafter, the solution of triphosgene in the second organic solvent is gradually introduced into the reactor (R-1) from the first tank (T-1). The introduction of the solution of triphosgene in the second organic solvent is carried out at a time or divided into two or more times. At that time, stirring is performed while the internal temperature of the reactor (R-1) is maintained to be constant. Upon completion of the introduction, an additional reaction is carried out while stirring is performed for a certain period of time. As an example, the color and transparency of the reaction solution are monitored with the naked eyes through a viewing window (G-1) provided in the reactor (R-1). As another example, the color and transparency of the reaction solution are measured with an optical device through the viewing window (G-1) provided in the reactor (R-1). The optical device may include a digital camera, a spectrometer, and optical analysis equipment.

The gas (second organic solvent, hydrogen chloride, phosgene, and the like) present inside the reactor (R-1) is transferred to a first condenser (C-1). In the first condenser (C-1), the second organic solvent is firstly condensed by cooling and recycled to the reactor (R-1), and the remaining gas is transferred to a second condenser (C-2). In the second condenser (C-2), the second organic solvent is secondly condensed by cooling and recycled to the reactor (R-1), and the remaining gas is transferred to a third condenser (C-3). In the third condenser (C-3), the second organic solvent is thirdly condensed by cooling and recycled to the reactor (R-1).

Once the second organic solvent is removed while it passes through the multi-stage condensers as described above, the remaining gas (hydrogen chloride, phosgene, and the like) is transferred to a first scrubber (S-1). In the first scrubber (S-1), hydrogen chloride gas is dissolved in water to obtain an aqueous hydrochloric acid solution and stored in a second tank (T-2), and the remaining gas is transferred to a second scrubber (S-2). In the second scrubber (S-1), phosgene ($COCl_2$) gas may be neutralized with an aqueous sodium hydroxide solution stored in a third tank (T-3) and removed.

The reaction solution obtained from the reactor (R-1) is sequentially transferred to a first distiller (D-1) and a second distiller (D-2). While it undergoes first and second distillation, the metaxylylene diisocyanate and the second organic solvent are separated from the reaction solution.

The second organic solvent separated from the reaction solution may be transferred to, and stored in, a solvent recovery apparatus (V-1). Thereafter, it may be recycled for the reaction of the metaxylylenediamine hydrochloride and triphosgene.

In addition, the metaxylylene diisocyanate separated from the reaction solution may be further subjected to filtration and drying to provide a final product.

[Process for Preparation of an Optical Lens]

The diisocyanate prepared in the above embodiment may be combined with other components to prepare a composition for an optical material. That is, the composition for an optical material comprises a diisocyanate prepared according to the above embodiment and a thiol or an episulfide. In addition, the composition for an optical material is mixed and heated and cured in a mold to produce an optical lens.

The process for preparing an optical lens according to an embodiment comprises preparing at least one diamine selected from the group consisting of orthoxylylenediamine, metaxylylenediamine, paraxylylenediamine, norbornenediamine, hydrogenated xylylenediamine, and isophoronediamine; reacting the diamine with an aqueous hydrochloric acid solution in a first solvent to obtain a diamine hydrochloride; reacting the diamine hydrochloride with triphosgene in a second organic solvent to obtain a diisocyanate; and mixing the diisocyanate with a thiol or an episulfide and polymerizing and curing the resultant in a mold.

The thiol may be a polythiol containing two or more SH groups. It may have an aliphatic, alicyclic, or aromatic skeleton. The episulfide may have two or more thioepoxy groups. It may have an aliphatic, alicyclic, or aromatic skeleton.

Specific examples of the thiol include bis(2-mercaptoethyl) sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl) sulfide, bis(2,3-dimercaptopropanyl) disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl) sulfide, bis(2-(2-mercaptoethylthio)-3-mercaptopropyl) disulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bispentaerythritol-ether-hexakis (3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptodimethylthio)ethyl)-1,3-dithiane, 2,5-bismercaptomethyl-1,4-dithiane, bis(mercaptomethyl)-3,6,9-trithiaundecan-1,11-dithiol.

Preferably, the thiol may be 2-(2-mercaptoethylthio)propane-1,3-dithiol, 2,3-bis(2-mercaptoethylthio)propane-1-thiol, 2-(2,3-bis(2-mercaptoethylthio)propylthio)ethanethiol, 1,2-bis(2-mercaptoethylthio)-3-mercaptopropane, 1,2-bis(2-(2-mercaptoethylthio)-3-mercaptopropylthio)-ethane, bis(2-(2-mercaptoethylthio)-3-mercaptopropyl) sulfide, 2-(2-mercaptoethylthio)-3-2-mercapto-3-[3-mercapto-2-(2-mercaptoethylthio)-propylthio]propylthio-propane-1-thiol, 2,2'-thiodiethanethiol, 4,14-bis(mercaptomethyl)-3,6,9,12,15-pentathiahectadecane-1,17-dithiol, 2-(2-mercaptoethylthio)-3-[4-(1-{4-[3-mercapto-2-(2-mercaptoethylthio)-propoxy]-phenyl}-1-methylethyl)-phenoxy]-propane-1-thiol, pentaerythritol tetrakis(3-mercaptopropionate), pentaerythritol mercaptoacetate, trimethanolpropanetrismercaptopropionate, glycerol trimercaptopropionate, dipentaerythritol hexamercaptopropionate, or 2,5-bismercaptomethyl-1,4-dithiane.

The thiol may be any one or two or more of the exemplary compounds, but it is not limited thereto.

In addition, specific examples of the episulfide include bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl) pentane, 1,6-bis(β-epithiopropylthio) hexane, 1-(β-epithiopropylthio)-5-(β-epithiopropylthiomethyl) hexane, 1-(β-epithiopropylthio)-2-[(2-β-epithiopropylthioethyl)thio]ethane, 1-(β-epithiopropylthio)-2-[[2-(2-β-epithiopropylthioethyl)thioethyl]thio]ethane, tetrakis(β-epithiopropylthiomethyl)methane, 1,1,1-tris(β-epithiopropylthiomethyl) propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-ditianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthiomethyl)-1,4-dithiane, 2,5-bis(β-epithiopropylthioethylthiomethyl)-1,4-dithiane, 1,3-bis(β-epithiopropylthio)benzene, 1,4-bis(β-epithiopropylthio)benzene, 1,3-bis(β-epithiopropylthiomethyl)benzene, 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, and 4,4'-bis(β-epithiopropylthio)biphenyl.

The episulfide may be any one or two or more of the exemplary compounds, but it is not limited thereto. In addition, the episulfide may be a compound in which at least one of the hydrogens of its thioepoxy group is substituted with a methyl group.

The composition for an optical material may comprise the diisocyanate and the thiol or episulfide in a mixed state or in a separated state. That is, in the composition, they may be in a state of being compounded in contact with each other or separated from each other so as not to contact each other.

The composition for an optical material may comprise the thiol or episulfide and the diisocyanate at a weight ratio of 2:8 to 8:2, 3:7 to 7:3, or 4:6 to 6:4.

A catalyst, a chain extender, a crosslinking agent, an ultraviolet stabilizer, an antioxidant, an anti-coloring agent, a dye, a filler, a release agent, and the like may be further added depending on the purpose when the composition for an optical material and an optical lens are prepared.

The thiol or episulfide is mixed with a diisocyanate and other additives, which is defoamed, injected into a mold, and gradually polymerized while the temperature is gradually elevated from low to high temperatures. The resin is cured by heating to prepare an optical lens.

The polymerization temperature may be, for example, 20° C. to 150° C., particularly 25° C. to 120° C. In addition, a reaction catalyst, which is conventionally used in the production of polythiourethane, may be employed in order to control the reaction rate. Specific examples of the reaction catalyst are as exemplified above.

In addition, if required, the optical lens thus prepared may be subjected to physical or chemical treatment such as anti-reflection coating, hardness, enhancements in abrasion resistance and chemical resistance, anti-fogging, surface polishing, antistatic treatment, hard coat treatment, anti-reflection treatment, and dyeing treatment.

The optical lens prepared by the above process has excellent optical properties such as transparency and refractive index. For example, the optical lens may have a refractive index of 1.60 or more, specifically a refractive index of 1.60 to 1.67. In addition, the optical lens may have an Abbe number of 30 to 50, specifically 30 to 45 or 31 to 40. In addition, the optical lens may have a light transmittance of 80% or more, 85% or more, or 87% or more, which may be a total light transmittance.

Mode for the Invention

Hereinafter, more specific embodiments are illustrated, but the present invention is not limited thereto.

<Preparation of a Diamine Hydrochloride>

Example 1

A 5-liter, 4-neck reactor was charged with 963.5 g (9.25 moles) of an aqueous solution of 35% hydrochloric acid, followed by lowering the internal temperature of the reactor to 15 to 20° C. with stirring. While the temperature of the reactor was maintained at 25 to 50° C., 600.0 g (4.4 moles) of metaxylylenediamine (m-XDA) was introduced for 1 hour. Upon completion of the introduction, the internal temperature of the reactor was lowered to 10 to 20° C., and it was stirred for 1 hour. Thereafter, 1,200.0 g of diethyl ether (Et$_2$O) as an organic solvent was introduced, and the internal temperature of the reactor was lowered to −5 to 0° C., followed by stirring for 30 minutes to 1 hour. Upon completion of the reaction, it was subjected to vacuum filtration using a filter, and the filtered diethyl ether was recovered for reuse. The recovery rate of the diethyl ether was 73%. Upon the vacuum filtration, metaxylylenediamine (m-XDA) hydrochloride was obtained. In order to remove the residual organic solvent and water, drying was performed under the conditions of a reactor external temperature of 90 to 100° C. and a vacuum pump of 0.1 Torr to obtain final metaxylylenediamine (m-XDA) hydrochloride. The m-XDA hydrochloride thus obtained was in a solid form of a pale yellow, the yield was 88%, and the water content was 2%.

Example 2

A 5-liter, 4-neck reactor was charged with 986.5 g (9.47 moles) of an aqueous solution of 35% hydrochloric acid, followed by lowering the internal temperature of the reactor to 15 to 20° C. with stirring. While the temperature of the reactor was maintained at 25 to 50° C., 600.0 g (4.4 moles) of m-XDA was introduced for 1 hour. Upon completion of the introduction, the internal temperature of the reactor was lowered to 10 to 20° C., and it was stirred for 1 hour. Thereafter, 1,260 g of isopropanol (i-PrOH) as an organic solvent was introduced, and the internal temperature of the reactor was lowered to −5 to 0° C., followed by stirring for 30 minutes to 1 hour. Upon completion of the reaction, it was subjected to vacuum filtration using a filter, and the filtered isopropanol was recovered for reuse. Here, the recovery rate of the isopropanol was 75%. Upon the vacuum filtration, m-XDA hydrochloride was obtained. In order to remove the residual organic solvent and water, drying was performed under the conditions of a reactor external temperature of 90 to 100° C. and a vacuum pump of 0.1 Torr to obtain final m-XDA hydrochloride. The m-XDA hydrochloride thus obtained was in a solid form of a pale yellow, the yield was 88%, and the water content was 2%.

Example 3

A 5-liter, 4-neck reactor was charged with 1,009.4 g (9.69 moles) of an aqueous solution of 35% hydrochloric acid, followed by lowering the internal temperature of the reactor to 15 to 20° C. with stirring. While the temperature of the reactor was maintained at 25 to 50° C., 600.0 g (4.4 moles) of m-XDA was introduced for 1 hour. Upon completion of the introduction, the internal temperature of the reactor was lowered to 10 to 20° C., and it was stirred for 1 hour. Thereafter, 1,320 g of tetrahydrofuran was introduced, and the internal temperature of the reactor was lowered to −5 to 0° C., followed by stirring for 30 minutes to 1 hour. Upon completion of the reaction, it was subjected to vacuum filtration using a filter, and the filtered tetrahydrofuran was recovered for reuse. The recovery rate of the tetrahydrofuran was 82%. Upon the vacuum filtration, m-XDA hydrochloride was obtained. In order to remove the residual solvent and water, drying was performed under the conditions of a reactor external temperature of 90 to 100° C. and a vacuum pump of 0.1 Torr to obtain final m-XDA hydrochloride. The m-XDA hydrochloride thus obtained was in a solid form of a pale yellow, the yield was 91%, and the water content was 3%.

Example 4

A 5-liter, 4-neck reactor was charged with 1,032.3 g (9.91 moles) of an aqueous solution of 35% hydrochloric acid, followed by lowering the internal temperature of the reactor to 15 to 20° C. with stirring. While the temperature of the reactor was maintained at 25 to 50° C., 600.0 g (4.4 moles) of m-XDA was introduced for 1 hour. Upon completion of the introduction, the internal temperature of the reactor was lowered to 10 to 20° C., and it was stirred for 1 hour. Thereafter, 1,440 g of isobutanol (i-BuOH) as an organic solvent was introduced, and the internal temperature of the reactor was lowered to −5 to 0° C., followed by stirring for 30 minutes to 1 hour. Upon completion of the reaction, it was subjected to vacuum filtration using a filter, and the filtered isobutanol was recovered for reuse. The recovery rate of the isobutanol was 82%. Upon the vacuum filtration, m-XDA hydrochloride was obtained. In order to remove the residual solvent and water, drying was performed under the conditions of a reactor external temperature of 90 to 100° C. and a vacuum pump of 0.08 Torr to obtain final m-XDA hydrochloride. The m-XDA hydrochloride thus obtained was in a solid form of a pale yellow, the yield was 92%, and the water content was 3%.

Example 5

A 5-liter, 4-neck reactor was charged with 1055.4 g (10.13 moles) of an aqueous solution of 35% hydrochloric acid, followed by lowering the internal temperature of the reactor to 15 to 20° C. with stirring. While the temperature of the reactor was maintained at 25 to 50° C., 600.0 g (4.4 moles) of m-XDA was introduced for 1 hour. Upon completion of the introduction, the internal temperature of the reactor was lowered to 10 to 20° C., and it was stirred for 1 hour. Thereafter, 1,500 g of methyl ethyl ketone (MEK) as an organic solvent was introduced, and the internal temperature of the reactor was lowered to −5 to 0° C., followed by stirring for 30 minutes to 1 hour. Upon completion of the reaction, it was subjected to vacuum filtration using a filter, and the filtered methyl ethyl ketone was recovered for reuse. The recovery rate of the methyl ethyl ketone was 82%. Upon the vacuum filtration, m-XDA hydrochloride was obtained. In order to remove the residual solvent and water, drying was performed under the conditions of a reactor external temperature of 90 to 100° C. and a vacuum pump of 0.05 Torr to obtain final m-XDA hydrochloride. The m-XDA hydrochloride thus obtained was in a solid form of a pale yellow, the yield was 92%, and the water content was 1%.

Comparative Example 1

The same reactor as in Example 1 was charged with 846 g of orthodichlorobenzene (ODCB) as a reaction solvent. 136.2 g (1.0 mole) of m-XDI and 621 g of ODCB were charged to the raw material tank (in a total amine concentration 8.5% by weight). Next, the internal temperature of the reactor was raised to 120° C. under atmospheric pressure. Thereafter, hydrogen chloride gas began to be introduced through the hydrogen chloride gas injection line. At the same time, the entire amount of the amine diluted with the solvent was introduced from the raw material tank by a raw material charging pump over 2 hours. Upon completion of the reaction, the obtained hydrochloride slurry (yield: 90%) had low fluidity, and a large amount of the hydrochloride was left in the reactor in the process of separating the hydrochloride.

Comparative Example 2

The same procedures as in Example 1 were repeated, except that a diamine hydrochloride was prepared without using an organic solvent (yield: 49%).

TABLE 1

|  | Ex. 1 | Ex. 2 | Ex. 3 | Ex. 4 | Ex. 5 | C. Ex. 1 | C. Ex. 2 |
|---|---|---|---|---|---|---|---|
| Aqueous hydrochloric acid solution | 963.5 g | 986.5 g | 1,009.4 g | 1,032.3 g | 1,055.3 g | HCl gas | 963.5 g |
| Internal temp. of the reactor | 20-50° C. | 20-50° C. | 20-50° C. | 20-50° C. | 20-50° C. | 120° C. | 20-50° C. |

TABLE 1-continued

|  | Ex. 1 | Ex. 2 | Ex. 3 | Ex. 4 | Ex. 5 | C. Ex. 1 | C. Ex. 2 |
|---|---|---|---|---|---|---|---|
| m-XDA | 600 g | 600 g | 600 g | 600 g | 600 g | 136.2 g | 600 g |
| Organic solvent | Et$_2$O 1,200 g | i-PrOH 1,260 g | THF 1,320 g | i-BuOH 1,440 g | MEK 1,500 g | ODCB 846 g + 621 g | — |
| Vacuum condition | 0.1 Torr | 0.1 Torr | 0.1 Torr | 0.08 Torr | 0.05 Torr | — | 0.1 Torr |
| Yield of hydrocholoride | 88% | 88% | 91% | 92% | 92% | 90% | 49% |
| Water content in hydrochloride | 2% | 2% | 3% | 3% | 1% | — | — |

<Preparation of a Diisocyanate>

Example 6

Once the inside of a 5-liter, 4-neck reactor had been purged with nitrogen, it was charged with 3,400 g of toluene. With stirring, 800 g of m-XDA hydrochloride finally obtained in Example 1 was slowly introduced thereto, followed by stirring while the inside of the reactor was maintained at 135° C. Thereafter, a solution in which 378.5 g of triphosgene (BTC) had been dissolved in 200 g of toluene was first introduced thereto over 10 to 14 hours, and a solution in which 378.5 g of BTC had been dissolved in 200 g of toluene was secondarily introduced thereto. Here, the internal temperature of the reactor was maintained at 135 to 140° C. The total time of introduction of the BTC solution was 33 hours. Upon completion of the introduction, an additional reaction was carried out for 3 to 4 hours. It was then cooled to a temperature of 90 to 110° C., and excess COCl$_2$ was purged with nitrogen to decompose. Upon completion of the reaction, it was subjected to first distillation at a temperature of 50 to 60° C. to remove toluene and second distillation at 120° C. to obtain metaxylylene diisocyanate (m-XDI). The recovery rate of toluene as a result of the first distillation was 85%. The m-XDI finally obtained had a purity of 99.5% and a yield of 84%.

Example 7

Once the inside of a 5-liter, 4-neck reactor had been purged with nitrogen, it was charged with 3,400 g of ethylbenzene. With stirring, 800 g of m-XDA hydrochloride obtained in Example 2 was slowly introduced thereto, followed by stirring while the inside of the reactor was maintained at 140° C. Thereafter, a solution in which 200 g of BTC had been dissolved in 200 g of ethylbenzene was first introduced thereto over 10 to 14 hours, and a solution in which 378.5 g of BTC had been dissolved in 200 g of ethylbenzene was secondarily introduced thereto. Here, the internal temperature of the reactor was maintained at 140 to 145° C. The total time of introduction of the BTC solution was 31 hours. Upon completion of the introduction, an additional reaction was carried out for 3 to 4 hours. It was then cooled to a temperature of 90 to 110° C., and excess COCl$_2$ was purged with nitrogen to decompose. Upon completion of the reaction, it was subjected to first distillation at a temperature of 50 to 60° C. to remove ethylbenzene and second distillation at 120° C. to obtain m-XDI. The recovery rate of ethylbenzene as a result of the first distillation was 85%. The m-XDI finally obtained had a purity of 99.7% and a yield of 86%.

Example 8

Once the inside of a 5-liter, 4-neck reactor had been purged with nitrogen, it was charged with 3,400 g of orthodichlorobenzene (ODCB). With stirring, 800 g of m-XDA hydrochloride obtained in Example 3 was slowly introduced thereto, followed by stirring while the inside of the reactor was maintained at 145° C. Thereafter, a solution in which 416.5 g of BTC had been dissolved in 200 g of ODCB was first introduced thereto over 10 to 14 hours, and a solution in which 416.5 g of BTC had been dissolved in 200 g of ODCB was secondarily introduced thereto. Here, the internal temperature of the reactor was maintained at 145 to 150° C. The total time of introduction of the BTC solution was 28 hours. Upon completion of the introduction, an additional reaction was carried out for 3 to 4 hours. It was then cooled to a temperature of 90 to 110° C., and excess COCl$_2$ was purged with nitrogen to decompose. Upon completion of the reaction, it was subjected to first distillation at a temperature of 50 to 60° C. to remove ODCB and second distillation at 120° C. to obtain m-XDI. The recovery rate of ODCB as a result of the first distillation was 88%. The m-XDI finally obtained had a purity of 99.8% and a yield of 90%.

Example 9

Once the inside of a 5-liter, 4-neck reactor had been purged with nitrogen, it was charged with 3,400 g of cyclohexane. With stirring, 800 g of m-XDA hydrochloride obtained in Example 4 was slowly introduced thereto, followed by stirring while the inside of the reactor was maintained at 145° C. Thereafter, a solution in which 454 g of BTC had been dissolved in 200 g of cyclohexane was first introduced thereto over 10 to 14 hours, and a solution in which 454 g of BTC had been dissolved in 200 g of cyclohexane was secondarily introduced thereto. Here, the internal temperature of the reactor was maintained at 145 to 150° C. The total time of introduction of the BTC solution was 30 hours. Upon completion of the introduction, an additional reaction was carried out for 3 to 4 hours. It was then cooled to a temperature of 90 to 110° C., and excess COCl$_2$ was purged with nitrogen to decompose. Upon completion of the reaction, it was subjected to first distillation at a temperature of 50 to 60° C. to remove cyclohexane and second distillation at 120° C. to obtain m-XDI. The recovery rate of cyclohexane as a result of the first distillation was 87%. The m-XDI finally obtained had a purity of 99.5% and a yield of 88%.

Example 10

Once the inside of a 5-liter, 4-neck reactor had been purged with nitrogen, it was charged with 3,400 g of monochlorobenzene. With stirring, 800 g of m-XDA hydrochloride obtained in Example 5 was slowly introduced thereto, followed by stirring while the inside of the reactor was maintained at 150° C. Thereafter, a solution in which 454 g of BTC had been dissolved in 200 g of monochlorobenzene was first introduced thereto over 12 hours, and a solution in which 454 g of BTC had been dissolved in 200 g of monochlorobenzene was secondarily introduced thereto. Here, the internal temperature of the reactor was maintained at 150 to 155° C. The total time of introduction of the BTC solution was 29 hours. Upon completion of the introduction, an additional reaction was carried out for 3 to 4 hours. It was then cooled to a temperature of 90 to 110° C., and excess $COCl_2$ was purged with nitrogen to decompose. Upon completion of the reaction, it was subjected to first distillation at a temperature of 50 to 60° C. to remove monochlorobenzene and second distillation at 120° C. to obtain m-XDI. The recovery rate of monochlorobenzene as a result of the first distillation was 86%. The m-XDI finally obtained had a purity of 99.6% and a yield of 90%.

Comparative Example 3

The temperature of the hydrochloride slurry of Comparative Example 1 in a reactor was elevated to 160° C. Phosgene gas was introduced through the hydrogen chloride gas injection line at 100 g/hr (1.0 mole/hr). The reaction was carried out for 8 hours while the temperature was maintained. Upon completion of the reaction, nitrogen was purged to remove unreacted phosgene gas and hydrogen chloride gas. Then, the reaction solution was filtered, and 8.2 g (dry weight) of unreacted hydrochloride was removed by filtration. The obtained filtrate was desolvated to obtain 183.3 g (yield converted from purity: 93.71% by mole) of m-XDI having of a purity of 96.2% and containing 1.1% by weight of impurities (CBi).

TABLE 2

|  | Ex. 6 | Ex. 7 | Ex. 8 | Ex. 9 | Ex. 10 | C. Ex. 3 |
|---|---|---|---|---|---|---|
| m-XDA hydrocholoride | Ex. 1 800 g | Ex. 2 800 g | Ex. 3 800 g | Ex. 4 800 g | Ex. 5 800 g | C. Ex. 1 Slurry |
| Organic solvent | 3,400 g of toluene | 3,400 g of ethylbenzene | 3,400 g of ODCB | 3,400 g of cyclohexane | 3,400 g of monochlorobenzene | — |
| Reactor Internal temp. | 135-140° C. | 140-145° C. | 145-150° C. | 145-150° C. | 150-155° C. | — |
| BTC | 757 g | 757 g | 833 g | 908 g | 908 g | Phosgene gas |
| Organic solvent | 400 g | 400 g | 400 g | 400 g | 400 g | — |
| Solvent recovery rate | 85% | 85% | 88% | 87% | 86% | — |
| Reaction temp. | >135° C. | >140° C. | >145° C. | >145° C. | >150° C. | — |
| Total introduction time | 33 hours | 31 hours | 28 hours | 30 hours | 29 hours | — |
| Yield of m-XDI | 84% | 86% | 90% | 88% | 90% | — |
| Purity (%) | 99.5% | 99.7% | 99.8% | 99.5% | 99.6% | 96.2% |

Example 8A

A process apparatus comprising a reactor having a viewing window as shown in FIG. 2 was constructed. The procedures of Example 8 were carried out in the apparatus to prepare m-XDI.

Once the inside of a 5-liter, 4-neck reactor had been purged with nitrogen, it was charged with 3,400 g of orthodichlorobenzene (ODCB). With stirring, 800 g of m-XDA hydrochloride obtained in Example 3 was slowly introduced thereto, followed by stirring while the inside of the reactor was maintained at 145° C. Thereafter, a solution in which 416.5 g of BTC had been dissolved in 200 g of ODCB was first introduced thereto over 10 to 14 hours, and a solution in which 416.5 g of BTC had been dissolved in 200 g of ODCB was secondarily introduced thereto. Here, the internal temperature of the reactor was maintained at 145 to 150° C. The total time of introduction of the BTC solution was 28 hours. Upon completion of the introduction, an additional reaction was carried out for 3 to 4 hours.

The color and transparency of the reaction solution in the reactor were observed with the naked eyes through the viewing window during the reaction. When the reaction solution was observed as transparent light brown, a part of the reaction solution was collected, and the color and transparency were analyzed precisely through an optical device to determine the timing for terminating the reaction.

Upon completion of the reaction, the reaction solution was then cooled to a temperature of 90 to 110° C., and excess $COCl_2$ was purged with nitrogen to decompose. Upon completion of the reaction, it was subjected to first distillation at a temperature of 50 to 60° C. to remove ODCB and second distillation at 120° C. to obtain m-XDI. The recovery rate of ODCB as a result of the first distillation was 88%. The m-XDI finally obtained had a purity of 99.8% and a yield of 90%.

Examples 8B and 8C

The same procedures as in Example 8A were carried out, except that the reaction equivalent, reaction temperature, or reaction time of m-XDA hydrochloride and BTC was changed to obtain reaction solutions of various colors and transparency, from which the final m-XDI was obtained in the same manner as in Example 8A.

The color and transparency of the reaction solutions obtained in the procedures of Examples 8A to 8C, and the yield and purity of the final m-XDI were measured. The results are shown in the table below. If the yield of m-XDI is 80% or more, it is expressed as ○, if it is less than 80%, it is expressed as ×. If the purity of m-XDI is 95% or more, it is expressed as ○, and if it is less than 95%, it is expressed as ×.

TABLE 3

|  | Example 8A | Example 8B | Example 8C |
| --- | --- | --- | --- |
| Transparency of a reaction solution | Transparent | Opaque | Transparent |
| Color of a reaction solution | Light brown | Light brown | Dark brown |
| Yield of m-XDI | ○ | × | ○ |
| Purity of m-XDI | ○ | ○ | × |

As can be seen from the above table, the color and transparency of the reaction solution of m-XDA hydrochloride and BTC were observed to determine the timing for terminating the reaction, whereby it was possible to enhance the efficiency of the process as well as the quality of the final product.

Composition for an Optical Material and Preparation of an Optical Lens

Examples 11 to 13

A first liquid containing meta-xylylene diisocyanate (m-XDI) prepared in Example 6 and a second liquid containing a thiol were mixed in the proportions shown in the table below to prepare a composition for an optical material.

TABLE 4

| Component (part by weight) | | Example 11 | Example 12 | Example 13 |
| --- | --- | --- | --- | --- |
| First solution | m-XDI | 52 | 46.92 | 50.09 |
|  | DBTC | 0.015 | 0.015 | 0.015 |
|  | Zelec ™ UN | 0.1 | 0.1 | 0.1 |
|  | Tinuvin ™ 329 | 0.05 | 0.05 | 0.05 |
| Second solution | GST | 48 | — | — |
|  | DMMD | — | 53.08 | — |
|  | BET | — | — | 49.41 |

DBTC: dibutyltin dichloride, catalyst, Aldrich
Zelec ™ UN: release agent, Aldrich
Tinuvin ™ 329: UV blocking agent, BASF
GST: 1,2-bis(2-mercaptoethyl)-3-mercaptopropane
DMMD: 2,5-bismercaptomethyl-1,4-dithiane
BET: bis(mercaptomethyl)-3,6,9-trithia-1,11-undecandithiol Examples 14 to 16

The compositions for an optical material of Examples 11 to 13 were cured to prepare optical lenses of Examples 14 to 16, respectively. The physical properties of the optical lenses thus prepared are shown in the table below.

TABLE 5

|  | Example 14 | Example 15 | Example 16 |
| --- | --- | --- | --- |
| Refractive index (nd20) | 1.66 | 1.66 | 1.66 |
| Abbe number (20° C.) | 32 | 32 | 32 |
| Specific gravity | 1.35 | 1.38 | 1.37 |
| Transmittance (%) | 91 | 91 | 91 |

As shown in the above table, the optical lenses prepared from the compositions for an optical material according to the Examples had a high refractive index and a high transmittance. Thus, they are suitable for use as an optical lens of high quality.

The invention claimed is:

1. A process for preparing metaxylylene diisocyanate, which comprises:
   reacting metaxylylenediamine with an aqueous hydrochloric acid solution in a first organic solvent to obtain metaxylylenediamine hydrochloride through a filtration, wherein the first organic solvent is a hydrophilic solvent; and
   reacting the metaxylylenediamine hydrochloride with triphosgene in a second organic solvent to obtain metaxylylene diisocyanate,
   wherein the reacting metaxylylenediamine with the aqueous hydrochloric acid solution sequentially comprises:
   (1a) introducing the aqueous hydrochloric acid solution to a first reactor;
   (1b) further introducing the metaxylylenediamine to the first reactor and stirring; and
   (1c) further introducing the first organic solvent to the first reactor and stirring,
   wherein the yield of the metaxylylene diisocyanate is 80% or more and the purity of the metaxylylene diisocyanate is 95% or more.

2. The process for preparing metaxylylene diisocyanate of claim 1, wherein the concentration of the aqueous hydrochloric acid solution is 20% by weight to 45% by weight.

3. The process for preparing metaxylylene diisocyanate of claim 1, wherein the metaxylylenediamine diamine and the aqueous hydrochloric acid solution are introduced to the reaction at an equivalent ratio of 1:2 to 5 at a temperature of 20° C. to 40° C.

4. The process for preparing metaxylylene diisocyanate of claim 1, wherein the metaxylylenediamine hydrochloride and triphosgene are introduced to the reaction at an equivalent ratio of 1:1 to 5, and the reaction of the metaxylylenediamine hydrochloride with triphosgene is carried out at a temperature of 130° C. to 160° C. for 5 hours to 100 hours.

5. The process for preparing metaxylylene diisocyanate of claim 1, wherein the first organic solvent is introduced to the reaction in an amount of 1 to 2 times the weight of the metaxylylenediamine, and the second organic solvent is introduced to the reaction in an amount of 3 to 5 times the weight of the metaxylylenediamine hydrochloride.

6. The process for preparing metaxylylene diisocyanate of claim 1, which further comprises removing the impurities generated in the step of obtaining the metaxylylenediamine hydrochloride together with the first organic solvent.

7. The process for preparing metaxylylene diisocyanate of claim 1, wherein the reaction of the metaxylylenediamine hydrochloride and triphosgene may sequentially comprise:
   (2a) introducing the second organic solvent to a second reactor;
   (2b) further introducing the metaxylylenediamine hydrochloride to the second reactor and stirring them; and (2c) further introducing triphosgene to the second reactor and stirring them.

8. The process for preparing metaxylylene diisocyanate of claim 1, wherein the metaxylylene diisocyanate is obtained as a result of subjecting the resultant of the reaction of the metaxylylenediamine hydrochloride and the triphosgene to first distillation at 40° C. to 60° C. for 2 to 8 hours and second distillation at 100° C. to 120° C. for 2 to 10 hours.

9. The process for preparing metaxylylene diisocyanate of claim 1, wherein the step of obtaining metaxylylene diisocyanate from the metaxylylenediamine hydrochloride and triphosgene comprise:
   (i) reacting the metaxylylenediamine hydrochloride with triphosgene in a second organic solvent to obtain a reaction solution;
   (ii) measuring the color and transparency of the reaction solution; and
   (iii) obtaining metaxylylene diisocyanate from the reaction solution.

10. The process for preparing metaxylylene diisocyanate of claim 9, wherein step (i) and step (ii) are simultaneously carried out, in which the timing for terminating the reaction of the metaxylylenediamine hydrochloride and triphosgene in step (i) is determined according to the color and transparency of the reaction solution measured in step (ii).

11. The process for preparing metaxylylene diisocyanate of claim 10, wherein the timing for terminating the reaction comes after when the reaction solution turns a transparent light brown color.

12. A process for preparing a diisocyanate, which comprises:
   preparing at least one diamine selected from the group consisting of orthoxylylenediamine, metaxylylenediamine, paraxylylenediamine, norbornenediamine, hydrogenated xylylenediamine, and isophoronediamine;
   reacting the diamine with an aqueous hydrochloric acid solution in a first organic solvent to obtain a diamine hydrochloride through a filtration, wherein the first organic solvent is a hydrophilic solvent; and
   reacting the diamine hydrochloride with triphosgene in a second organic solvent to obtain a diisocyanate,
   wherein the reacting the diamine with the aqueous hydrochloric acid solution sequentially comprises:
   (1a) introducing the aqueous hydrochloric acid solution to a first reactor;
   (1b) further introducing the diamine to the first reactor and stirring; and
   (1c) further introducing the first organic solvent to the first reactor and stirring,
   wherein the yield of the metaxylylene diisocyanate is 80% or more and the purity of the metaxylylene diisocyanate is 95% or more.

13. The process for preparing a diisocyanate of claim 12, wherein the diisocyanate is at least one selected from the group consisting of orthoxylylene diisocyanate, metaxylylene diisocyanate, paraxylylene diisocyanate, norbornene diisocyanate, hydrogenated xylylene diisocyanate, and isophorone diisocyanate, and has a purity of 99.5% or more.

14. A process for preparing an optical lens, which comprises:
   preparing at least one diamine selected from the group consisting of orthoxylylenediamine, metaxylylenediamine, paraxylylenediamine, norbornenediamine, hydrogenated xylylenediamine, and isophoronediamine;
   reacting the diamine with an aqueous hydrochloric acid solution in a first organic solvent to obtain a diamine hydrochloride through a filtration, wherein the first organic solvent is a hydrophilic solvent;
   reacting the diamine hydrochloride with triphosgene in a second organic solvent to obtain a diisocyanate; and
   mixing the diisocyanate with a thiol or an episulfide and polymerizing and curing the resultant in a mold,
   wherein the reacting the diamine with the aqueous hydrochloric acid solution sequentially comprises:
   (1a) introducing the aqueous hydrochloric acid solution to a first reactor;
   (1b) further introducing the diamine to the first reactor and stirring; and
   (1c) further introducing the first organic solvent to the first reactor and stirring,
   wherein the yield of the metaxylylene diisocyanate is 80% or more and the purity of the metaxylylene diisocyanate is 95% or more.

* * * * *